(12) United States Patent
Taylor et al.

(10) Patent No.: US 11,060,067 B2
(45) Date of Patent: Jul. 13, 2021

(54) HUMAN LIVER MICROPHYSIOLOGY PLATFORM AND SELF ASSEMBLY LIVER ACINUS MODEL AND METHODS OF THEIR USE

(71) Applicants: D. Lansing Taylor, Pittsburgh, PA (US); Albert Gough, Glenshaw, PA (US); Larry Vernetti, Wexford, PA (US)

(72) Inventors: D. Lansing Taylor, Pittsburgh, PA (US); Albert Gough, Glenshaw, PA (US); Larry Vernetti, Wexford, PA (US)

( * ) Notice: Subject to any disclaimer, the term of this patent is extended or adjusted under 35 U.S.C. 154(b) by 551 days.

(21) Appl. No.: 15/515,837

(22) PCT Filed: Sep. 30, 2015

(86) PCT No.: PCT/US2015/053361
§ 371 (c)(1),
(2) Date: Mar. 30, 2017

(87) PCT Pub. No.: WO2016/054288
PCT Pub. Date: Apr. 7, 2016

(65) Prior Publication Data
US 2017/0292117 A1 Oct. 12, 2017

Related U.S. Application Data

(60) Provisional application No. 62/057,625, filed on Sep. 30, 2014.

(51) Int. Cl.
*C12N 5/071* (2010.01)
*C12M 3/06* (2006.01)
*C12M 1/42* (2006.01)
*B01L 3/00* (2006.01)
*G01N 33/50* (2006.01)

(52) U.S. Cl.
CPC ...... *C12N 5/0697* (2013.01); *B01L 3/502715* (2013.01); *B01L 3/502761* (2013.01); *C12M 23/16* (2013.01); *C12M 35/08* (2013.01); *C12N 5/067* (2013.01); *G01N 33/5067* (2013.01); *G01N 33/5082* (2013.01); *B01L 2300/0636* (2013.01); *C12N 2502/11* (2013.01); *C12N 2502/14* (2013.01); *C12N 2502/28* (2013.01); *C12N 2510/00* (2013.01); *C12N 2513/00* (2013.01); *C12N 2533/50* (2013.01); *C12N 2533/54* (2013.01)

(58) Field of Classification Search
None
See application file for complete search history.

(56) References Cited

U.S. PATENT DOCUMENTS

| | | | | |
|---|---|---|---|---|
| 5,827,729 A | * | 10/1998 | Naughton | A61F 2/022 435/297.2 |
| 6,004,810 A | * | 12/1999 | Tateno | C12N 5/0672 435/353 |
| 6,472,200 B1 | * | 10/2002 | Mitrani | A61M 1/34 435/284.1 |
| 6,737,270 B1 | * | 5/2004 | Michalopoulos | A61L 27/3804 424/93.7 |
| 2002/0182188 A1 | * | 12/2002 | Reid | A61P 1/00 424/93.21 |
| 2002/0188240 A1 | * | 12/2002 | Gorsuch | A61M 1/3679 604/6.04 |
| 2003/0096411 A1 | * | 5/2003 | Michalopoulos | A61L 27/3804 435/373 |
| 2003/0129736 A1 | * | 7/2003 | Mitrani | A61M 1/1678 435/284.1 |
| 2005/0049581 A1 | * | 3/2005 | Gerlach | C12M 23/58 606/1 |
| 2007/0148767 A1 | | 6/2007 | Yang et al. | |
| 2011/0159522 A1 | | 6/2011 | Kamm et al. | |
| 2012/0182609 A1 | * | 7/2012 | Borenstein | B01L 3/502707 359/368 |
| 2016/0032239 A1 | * | 2/2016 | Livermore-Clifford | A61L 27/3886 435/395 |
| 2018/0258400 A1 | * | 9/2018 | Ng | C12N 5/0672 |
| 2019/0093077 A1 | * | 3/2019 | Hamilton | C12M 23/16 |
| 2020/0254447 A1 | * | 8/2020 | Lockman | B01L 3/502707 |

FOREIGN PATENT DOCUMENTS

WO 2006127768 A2 11/2006
WO WO 2006127768 * 11/2006 ............... C12N 5/08

OTHER PUBLICATIONS

Sevilla, Carlos "The Role of Extracellular Matrix Fibronectin and Collagen in Cell Proliferation and Cellular Self-Assembly", 2012, Department of Biomedical Engineering, University of Rochester.*
Sevilla, The Role of Extracellular Matrix Fibronectin and Collagen in Cell Proliferation and Cellular Self-Assembly, Theses, University of Rochester, 2012, pp. 1-179 [retrieved on Jan. 13, 2016, from https://urresearch.rochester.edu/institutionalPublicationPublicView.action?institutionalItemId=27206&versionNumber=1] p. 136, para 2; p. 139, para 1.
International Search Report and Written Opinion for International application No. PCT/US2016/053361, dated Feb. 4, 2016.

* cited by examiner

*Primary Examiner* — Ann Y Lam
(74) *Attorney, Agent, or Firm* — Troutman Pepper Hamilton Sanders LLP

(57) ABSTRACT

Microfluidic devices for modeling three-dimensional tissue structures and methods for making and using the same are described herein.

23 Claims, 15 Drawing Sheets

HUMAN LIVER MICROPHYSIOLOGY PLATFORM AND SELF ASSEMBLY LIVER ACINUS MODEL AND METHODS OF THEIR USE

CROSS-REFERENCE TO RELATED APPLICATIONS

This application is a U.S. national stage filing under 35 U.S.C. § 371 of International application Ser. No. PCT/US2015/053361 entitled "A Human Liver Microphysiology Platform And Self Assembly Liver Acinus Model And Methods Of Their Use," and filed on Sep. 30, 2015, which claims benefit of and priority under 35 U.S.C. § 119(e) to U.S. Provisional Application No. 62/057,625 entitled "A Human Liver Microphysiology Platform And Self Assembly Liver Acinus Model And Methods Of Their Use," filed Sep. 30, 2014. The contents of each of these applications are incorporated herein by reference in their entireties.

STATEMENT OF GOVERNMENT INTEREST

The United States Government may have certain rights to this invention pursuant to Grant No. 1UH2TR00503-01 entitled "A 3D Biomimetic Liver Sinusoid Construct for Predicting Physiology and Toxicity" awarded by the National Institutes of Health.

BACKGROUND

In drug discovery, as well as industrial and environmental health and safety, there is a significant need for lower cost, easy-to-use, robust, high-throughput biological models that predict human safety and efficacy. Four major issues have limited the success of liver models as predictors of pharmacokinetics (PK), toxicity and efficacy in humans: 1) lab animal models correlate poorly (~50%) with human liver drug effects; 2) human liver tissue is difficult to obtain and usually of variable quality; 3) simple 2D models do not replicate key functions associated with liver failure, such as fibrosis and the immune response; and 4) in vitro models have exhibited a short functional lifetime (~2 weeks) that excludes some chronic effects.

Recently established surgical research networks and cryopreservation techniques have improved the quality of available human cells. In addition, significant progress has been made in developing induced pluripotent stem cells (hereafter, "iPSC's") into adult hepatocytes. The ability to put patient-specific cells into this in vitro model will dramatically expand its power to investigate liver diseases such as nonalcoholic fatty liver disease, infectious diseases, liver cancer and a niche site for metastatic breast cancer, as well as use in targeted drug discovery and safety testing. Combined with recent developments in microfluidics, we are now able to construct an all human-cell, self-assembly, 3D, microfluidic model of the liver that can be maintained for at least a month, referred to here as the self-assembly liver acinus (SALA) model. In addition, a whole human liver microphysiology platform (HLMP) has been developed that includes the SALA model in a microfluidic device, fluorescence-based biosensors for real-time measurements, and a database for management, processing, and computational modeling of large and complex data sets. The SALA model and platform (HLMP) disclosed here are novel in the use of multiple human cell types that self-assemble into an organ model that maintains many organizational and functional features of the liver in a microfluidic device that allows imaging analysis of cellular responses using genetically engineered biosensors.

The media flow through the model provides physiological flow properties, and a means for delivering both nutrients and test compounds. The efflux media provides an opportunity to measure standard clinical biomarkers and mass spectrometry analysis of compound metabolism. The multiparameter data generated by the model is accumulated in a database, where it is correlated with published data from preclinical, clinical and post-market drug trials, in order to construct classifiers that will predict human organ interactions. The SALA and HLMP comprise the cells, the microfluidic device, the media and other reagents, the biosensors, the image analysis algorithms, the Microphysiology database, and the predictive models. This model and platform have the potential to revolutionize safety testing by providing a 3D microphysiology liver that responds to compound exposure with many of the same mechanisms as a human liver, while allowing direct imaging of those mechanisms in "sentinel" cells with integrated biosensors, along with measurement of standard clinical biomarkers, to generate data in vitro that is predictive of in vivo pharmacokinetics, pharmacodynamics (PK/PD), and efficacy testing in disease models.

SUMMARY

Embodiments of the invention are directed to a microfluidic device including a housing having at least one inlet and at least one outlet, extracellular matrix proteins disposed on at least one surface of the housing, cells of at least two types associated with the extracellular matrix proteins forming three-dimensional structures within the housing; and a flow medium contacting the cells. In some embodiments, the cells of at least two types may be primary liver cells, cultured liver cells, induced pluripotent stem cells, primary hepatocytes, endothelial cells, immune cells, stellate cells, and combinations thereof. In certain embodiments, the cells of at least to types may be human hepatocytes, human endothelial cells, human immune cells, and human stellate cells. In particular embodiments, the cells may further include genetically modified cells expressing a genetically encoded fluorescence based biosensors, and the genetically encoded fluorescence based biosensor may dependent upon, for example, calcium levels, pH, glutathione levels, mitochondrial calcium levels, oxidative stress, or reactive oxygen species. In particular embodiments, expression of the genetically encoded fluorescence based biosensor may be in response to apoptosis, change in mitochondrial membrane potential, cell proliferation, free calcium ion concentration, cell motility, and oxidative stress response. In certain embodiments, the three-dimensional structures may exhibit zonation, and in some embodiments, the three-dimensional structures may be liver acini.

In some embodiments, the microfluidic device may further include a pump fluidly connected to the inlet configured to propel flow medium through the housing. In various embodiments, the housing may include one or more chambers and one or more passages fluidly connecting the chambers, and in some embodiments, the extracellular matrix proteins may be disposed in the chambers of the housing. In particular embodiments, the microfluidic device may further include a sensor positioned to detect analytes in effluent exiting the housing, and in some embodiments, the microfluidic device may further include an imager positioned to image the three-dimensional structures. In further embodiments, the microfluidic device may include one or more ports positioned to introduce substances into the flow medium.

Other embodiments are directed to a method for self-assembly of liver acini including the steps of providing a surface coated with an extracellular matrix protein; contacting the surface with hepatocytes; incubating the surface for about 12 to about 16 hours; contacting the surface with endothelial cells, immune cells, or combinations thereof; incubating the surface for about 1 to about 12 hours; and contacting the surface with polymerized collagen. The surface may be disposed within a microfluidic device. In some embodiments, contacting the surface with polymerized collagen may include introducing collagen into the microfluidic device; inverting the microfluidic device; polymerizing the collagen; and inverting the microfluidic device. In various embodiments, the hepatocytes may include genetically modified hepatocytes expressing a genetically encoded fluorescence based biosensors.

DETAILED DESCRIPTION

Figure 1:
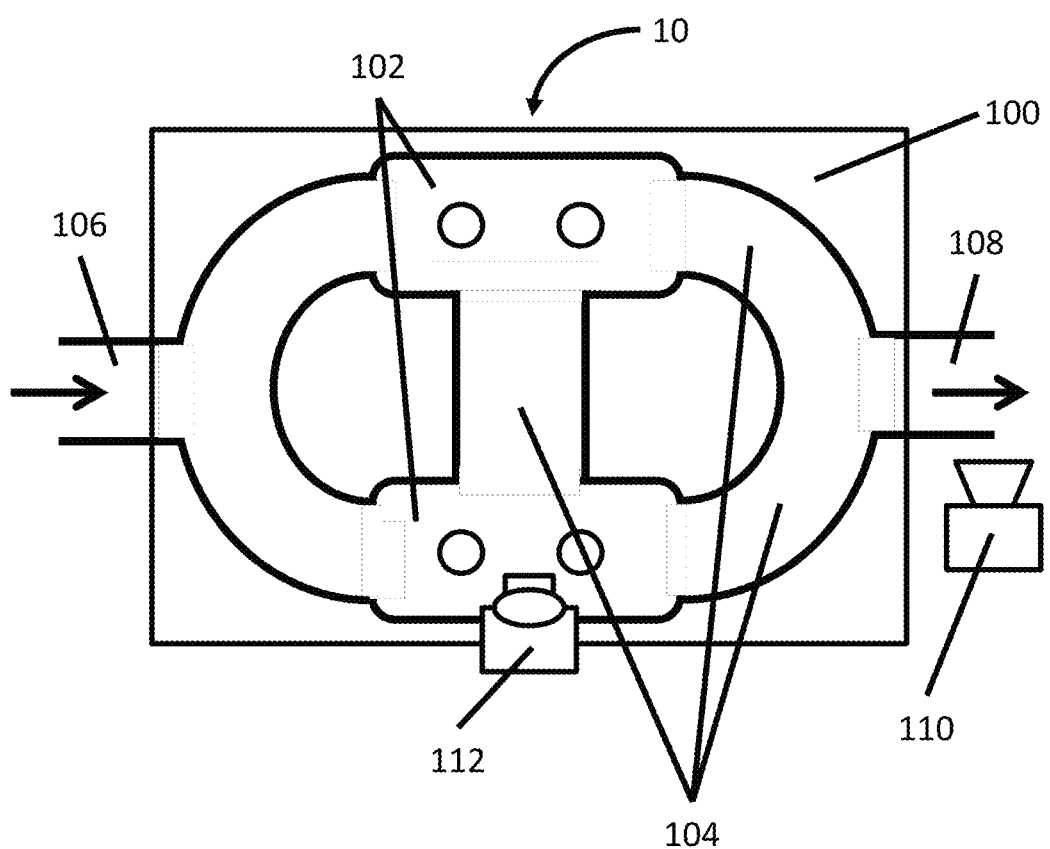
FIG. 1 is a diagram of a microfluidic device.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity.

It will be understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

Embodiments of the invention are directed to microfluidic device including a self-assembled liver acinus, and methods for using such microfluidic devices for in vivo pharmacokinetics, pharmacodynamics (PK/PD), and efficacy testing in disease models. In various embodiments, the microfluidic device may include a housing and multiple human cell types and a flow of medium disposed within the housing. In some embodiments, the microfluidic device may include other components that reflect in vivo biology of the liver or other organs disposed within the housing. The microfluidic device may further include a variety of sensors positioned to detect discharged biomaterials such as metabolites and other compositions produced by the cells in the microfluidic device over time. The methods of various embodiments may generally include the steps of introducing a compound or composition under study into the microfluidic device and detecting discharged biomaterials. In some embodiments, the device may include a computer or other means for analyzing the detected discharged biomaterials. Thus, embodiments of the method include identifying the discharged biomaterials. The microfluidic device may function for one month or more to measure chronic effects on toxicity and disease progression.

A diagram showing an example of the microfluidic devices of various embodiments is provided in FIG. 1. The microfluidic device 10 of FIG. 1 includes a housing 100 having various fluidly connected chambers 102 and passages 104. The housing 100 of various may be clear for imaging the cells and tissues in the microfluidic device, or at least a portion of the housing may be clear. In some embodiments, the housing 100 may include upper and lower substrates and either the upper or lower or both the upper and lower substrates may be optically transparent, i.e., clear. In other embodiments, the housing may include transparent windows are various locations allowing for observation of the cells and tissues enclosed within the housing at those locations. The housing may include one or more passages 104 for cellular adhesion and tissue growth, and in some embodiments, the housing may include one or more chambers 102 connected by passages 104. The chambers 102 may be configured to support tissue growth. For example, the chambers 102 may be coated with collagen or other extracellular matrix components that facilitate adherence of cells of various tissue types to surfaces of the chambers. Passages 104 may not include such coatings to discourage cell adherence and growth to maintain flow of flow medium. The passages 104 and chambers 102 of various embodiments may be configured to provide a continuous flow of flow medium from an inlet 106 to an outlet 108 of the device.

In some embodiments, the microfluidic device may be self-contained (not depicted) meaning that the cells, extracellular matrix proteins, and flow medium are loaded into the microfluidic device, and the microfluidic device is sealed creating a closed system. In other embodiments, the microfluidic device 10 may have at least one inlet 106 and at least one outlet 108 through which flow medium may be added to or removed from the microfluidic device, which contains established living human cells. In certain embodiments, the microfluidic device 10 may mimic directional blood flow and provide an in vivo-like route of drug administration, nutrient delivery, and oxygen replenishment, necessary for establishing metabolic zonation and an elimination route for metabolic waste and other secretions. Such a flow may provide an efflux media for standard clinical measurements of organ function, for example, albumin and urea synthesis, and evidence of drug challenge such as enzyme secretion, drug clearance, and metabolites.

In some embodiments, the microfluidic device 10 may include one or more sensors 110 configured to monitor discharged biomaterials created from materials introduced into the microfluidic device. For example, in some embodiments, a drug or potentially therapeutic compound can be introduced into the microfluidic device, and the one or more sensors 110 may be configured to detect drug metabolites and other biochemical by-products produced as a result of the introduction of the drug into the device in an efflux media. In such embodiments, the microfluidic device 10 may provide a means for testing the effect of the drug on specific tissue types such as liver acini. Embodiments are not limited to particular sensors 110, and the microfluidic device may include sensors such as, biochemical, mass spectroscopy, fluorescence-based biosensors, and the like and combinations thereof. Such sensors may generally be non-destructive meaning they do not physically touch the cells or extracellular matrix proteins in the microfluidic device. In certain embodiments, such non-destructive sensors may include optical sensors such as those typically used for secretion assays. In particular embodiments, the sensors may be real-time meaning that the device identifies and/or measures the discharged biomaterials as they are discharged into the flow medium, and in some embodiments, the sensors may provide quantitative high content analysis (HCA) optical read-outs. In certain embodiments, the microfluidic device 10 may monitor any of the various cell types disposed within the microfluidic device individually or in user-defined combinations.

In some embodiments, the microfluidic device 10 may include one or more imaging devices 112 positioned to capture images of the cells and tissues disposed within the housing 100. The imaging device 112 may be in a fixed position, and in other embodiments, the imaging device 112 may be movable.

The microfluidic device 10 may include any number of cells of various types, which may be chosen to mimic particular tissue-types, and in some embodiments, the microfluidic device may include extracellular matrix proteins or other components of the organ of interest that allow the cells to organize into the particular tissue-type. For example, in some embodiment, the microfluidic device may include liver cells and a mixture of extracellular matrix proteins disposed within the housing of the microfluidic device. In some embodiments, the extracellular matrix proteins may self-assembly into three-dimensional scaffolding necessary to produce the tissue, such as liver acini. In other embodiments, the housing may include a projections or other surfaces onto which the extracellular matrix proteins can adhere to produce the three-dimensional architecture necessary to mimic the tissue type of interest. In certain embodiments, the microfluidic device may be configured to mimic liver tissue, and the extracellular matrix proteins may be selected from extracellular matrix proteins necessary to produce liver acini. One or more types of liver cells may be adhered to the extracellular matrix proteins to form the acini, and in particular embodiments, at least four human liver cell types may be contained within the microfluidic device to mimic acini. In certain embodiments, the human liver cells may be derived from a patient.

In example embodiments, the cells contained within the microfluidic device may be replatable cryopreserved human hepatocytes. In other example embodiments, the cells contained within the microfluidic device may be hepatocytes and three non-parenchymal cell (NPC) established human cell culture lines for the endothelial, immune, and stellate cells. These cell types can be chosen for expression of particular phenotypes. For example, in some embodiments, the microfluidic device may include LX-2 stellate cells that express human collagen necessary for the fibrotic scarring and U937 monocytic cells that expresses receptors necessary for immune mediated toxicity. In certain embodiments the cells contained within the microfluidic device may be cells derived from patients. Various patients having different genetic backgrounds may be used to source the cells. For example, the microfluidic devices of various embodiments may contain cells from patients having normal liver function or patients having non-alcoholic fatty liver disease, cancer, or other liver specific diseases. Such microfluidic devices may provide, as well as toxic response to drugs different will permit specific disease models such as.

In some embodiments, human iPSC can be incorporated into the microfluidic device, and in certain embodiments, the iPSC can be differentiated from a pluripotent state into hepatocytes. iPSC is a renewable cell source that can be easily obtained from academic labs, public cell banks and commercial vendors. iPSC allow for genotype-specific studies (including individual patients) to be performed routinely, since the cells are sourced from individual child or adult donors. Further, the iPSC can be modified by established and emerging genetic engineering techniques such that the integration of biosensors can be specifically targeted within the cell genome.

In some embodiments, the tissue contained within the microfluidic device may exhibit zonation. For example, in liver models, functional gradient or metabolic zonation of the hepatocytes can be established along the acinar sinusoidal units. Different functions (e.g., protein synthesis, ammonia detoxification, drug metabolism) are carried out in the various metabolic zones which can lead to unintentional site specific drug toxicity. For example, acetaminophen exhibits site specific drug toxicity. Zonation can be measured with existing sensors for oxygen and pH across the long dimension of the device.

Certain embodiments are directed to methods for establishing tissue types in a microfluidic device, and such method may include "self-assembly," which refers to spontaneous formation of tissue-like organization. In some embodiments, the method may include of step of introducing hepatocytes into the microfluidic device having one or more internal compartments having one or more surfaces that are coated with collagen or another extracellular matrix protein that allows adherence of the hepatocytes to the microfluidic device. The hepatocytes attach to the collagen coated surfaces. In some embodiments, the hepatocytes may be incubated in the microfluidic device for about 12 to about 16 hours. During this time, the hepatocytes may form in vivo-like 'cords' or rows of 2-4 hepatocytes that vary in width and length and cover the surfaces of the device. See FIG. 2. The method may further include introducing endothelial cells, immune cells, and combinations thereof into the microfluidic device after the hapatocytes have been incubated. Endothelial cells adhere to and spread over the hepatocytes and may infiltrate the spaces between the hepatocyte cords. In some embodiments, the microfluidic device may be incubated for about 1 to about 12 hours after introducing endothelial cells and/or immune cells into the microfluidic device. After incubating the endothelial and/or immune cells, the method may include the step of introducing a preparation of viscous collagen type-1 into the microfluidic device. Such preparations may include stellate cells. In particular embodiments, the method may include polymerizing the collagen into a rigid state by inverting the device after introducing the collagen preparation to maintain a separation between the stellate cells and hepatocytes, immune, and endothelial cells. See FIG. 2. After polymerizing has occurred, the method may include contacting the hepatocytes, immune, and endothelial cells by inverting device to produce self-assembled tissue. See FIG. 2. The microfluidic device may then be attached to a microfluidic pump for the application of flow medium over the self-assembled tissue.

In some embodiments, the method may include flowing flow medium through the microfluidic device with self-assembled tissue for about 1 to about 14 days. During this time the cell types migrate and self-assemble into distinct layers forming liver like tissue. The layers may include hepatocytes attached to the surfaces of the device in cord formations. Stellate cells may migrate to the hepatocyte layer, and endothelial cells may leave the hepatocyte layer to form a loose interconnected layer above the hepatocytes. This arrangement has similarities to the organization and architecture of the liver sinusoidal unit, a fundamental component of liver organization and function.

Figure 2:
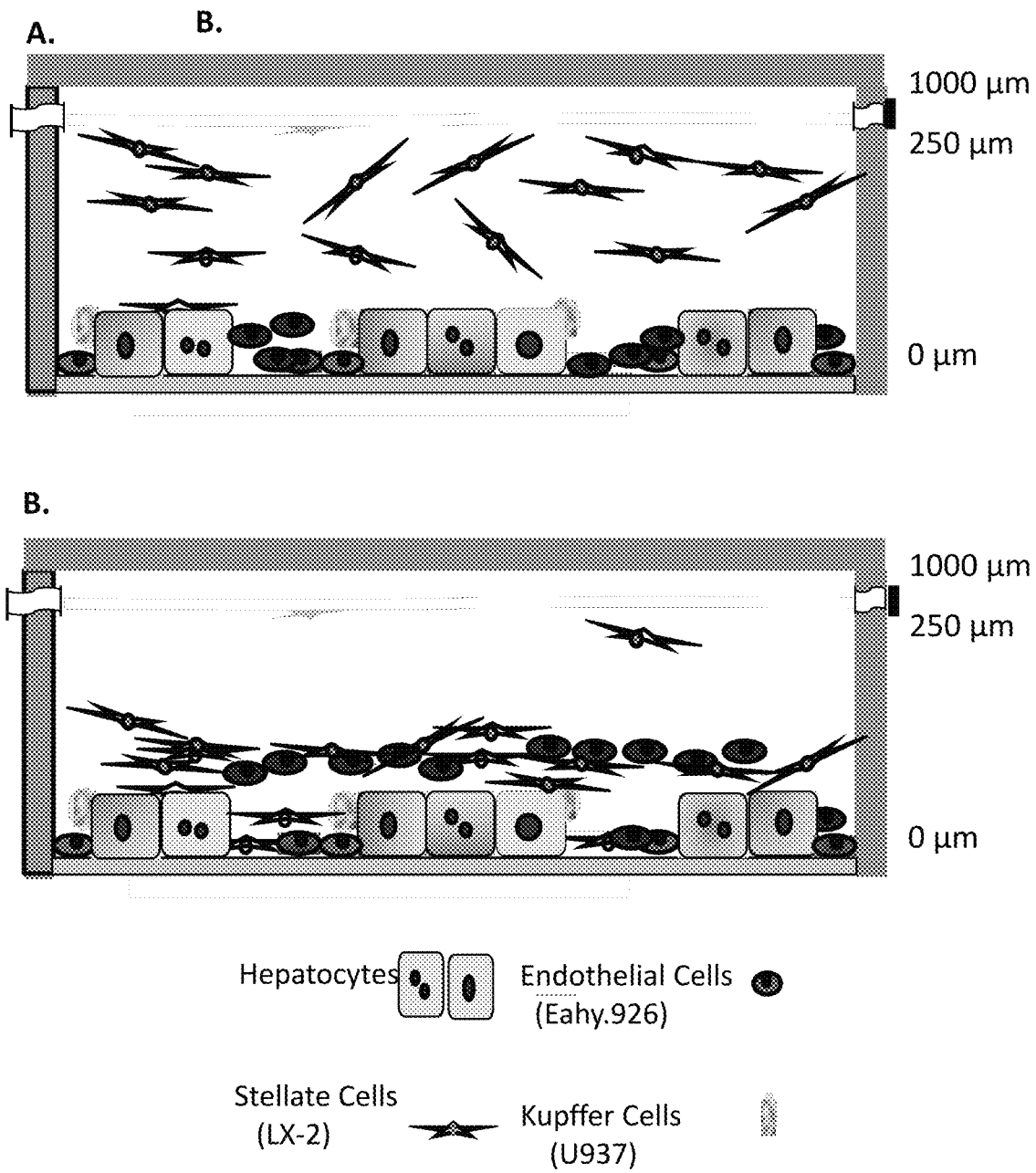
FIG. 2 is a diagram showing self-assembly of three-dimensional liver tissue in the SALA model.

The microfluidic devices of various embodiments may have a similar architecture to that described above. For example, in certain embodiments, the microfluidic devices described above may include hepatocytes attached to the surfaces of the device in cord formations, stellate cells associated with the hepatocyte layer, and endothelial cells in a loose interconnected layer above the hepatocytes as depicted in FIG. 2. The four human cell types discussed above contribute to liver health, and therefore toxicity response and disease phenotype. In particular embodiments, human hepatocytes (primary or iPSC-derived), human endothelial cells (EAhy.926 or similar or primary), human immune cells (monocytes U937 or similar or primary), and human stellate cells (LX-2 or similar or primary) may be used in particular embodiments of the invention, although other cell types may be incorporated into the microfluidic devices to reproduce other tissue types. In such embodiments, the primary hepatocytes may retain metabolic capacity not found in immortalized hepatic cell lines. Human stellate cells reproduce fibrotic liver scarring, and immune cells reproduce immune-mediated tissue damage both important mechanisms of toxicity.

FIG. 2 shows the organization of cells as discussed above. Panel a shows a cross-section diagram based on confocal images of the typical cell organization on day 1 after cell seeding of the hepatocytes, Kupffer immune cells (U937), endothelial (EAhy.926) and Stellates (LX-2). Hepatocytes are first seeded on a layer of collagen. Endothelial cells and U937 are seeded 18-24 hours after hepatocytes and initially localize between the hepatocytes. LX-2 Stellates are seeded and are initially, evenly dispersed in the collagen layer. Panel B shows a diagram of typical cell organization 7 days after cell seeding, when endothelial cells and Stellate cells are localized both between hepatocytes and in a layer above the hepatocytes. The schematics in panels A and B of FIG. 2 were abstracted from the scans of 26 image planes 10 µm apart starting at the hepatocyte layer.

Figure 3:
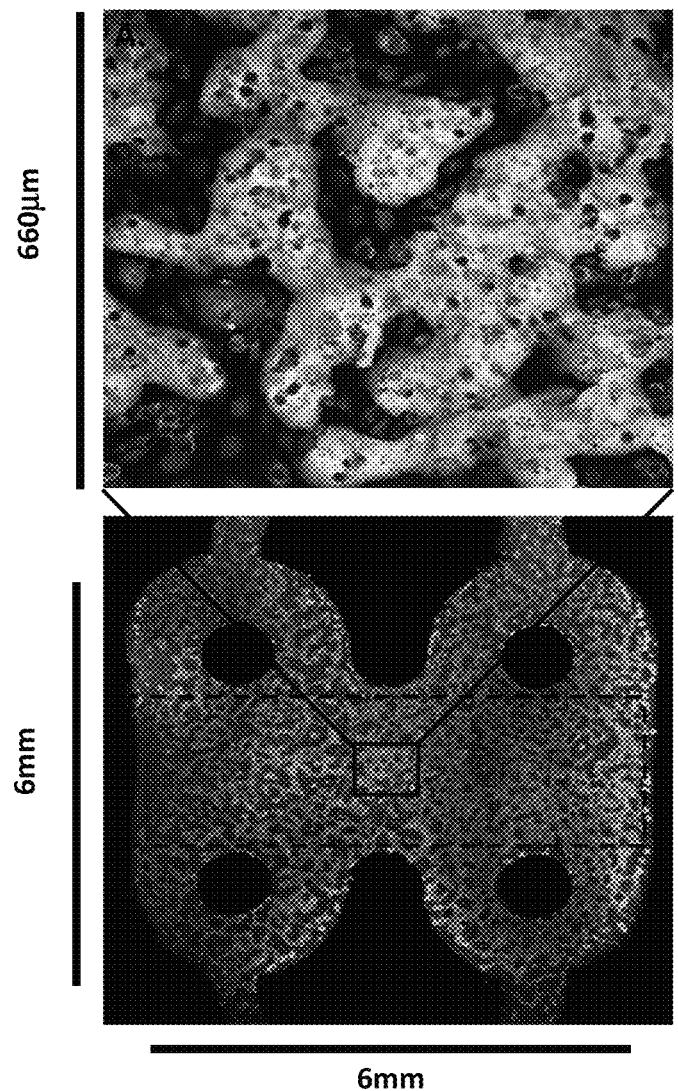
FIG. 3 are fluorescence micrographs of a microfluidic device including self-assembled three-dimensional liver tissue in the SALA model.

FIG. 3 show confocal images of a microfluidic device in which a subset of the total seeded cells (~20%) are sentinel cells stably expressing a fluorescence-based biosensor and the remaining cells are unmodified. In panel A, primary hepatocytes self-organized into cords by day 7 are identified by inhibiting cannicular transport of a dye (CMFDA, green). The other cell types self-assemble relative to the hepatocytes. Mitochondria are labelled with TMRE (red) and cell nuclei with hoechst (blue). In panel B, labeled hepatocyte chords (CMFDA, green). The cells are under constant flow at ca. 5 µl/hr with the influx port at the top and the efflux at the bottom. The red box represents the size of a 20X field shown in panel A within the chamber and the dashed yellow box shows the region from which multiple image fields were collected. Approximately 200,000 total cells are present in the entire chamber, added in physiological ratios of hepatocytes and non-parenchymal cells.

The microfluidic devices of various embodiments may include a flow pump associated with an inlet to the housing and an outlet that allow flow media to leave the microfluidic device. In some embodiments, the pump may draw flow medium from a primary reservoir and pump the flow media through the inlet into the housing where the flow medium can contact the cells and tissues in the microfluidic device. The flow media may exit the microfluidic device through an outlet port. The outlet port may be associated with a second reservoir where flow medium is collected or sample reservoirs, where samples are collected. In some embodiments, the flow medium may be collected in the primary reservoir and pumped back into the microfluidic device. In such embodiments, the flow medium may be mixed with nutrients and other materials necessary to maintain the cells and tissues in the microfluidic device before being pumped back through the device. Flow of flow media is important for maintaining cells in 3D tissue and tissue models, to induce in vivo-like organization and function, including oxygen zonation, and to deliver reagents to the cells. In some embodiments, the microfluidic devices may include one or more ports to load cells and introduce nutrients, drugs, test substances, and other materials into the microfluidic device without modifying the flow of flow media through the device.

The loss of hepatocyte functionality occurs within days in the absence of additional cell types and a biological matrix such as collagen. The unique combination of cell types, extracellular matrix proteins and flow through culture conditions in the invention has demonstrated retention of hepatocyte cell polarity and metabolism for up to 28 days (See figures in associated document). The ability of the SALA model to maintain function long-term allows for detection of chronic drug toxicities and disease phenotypes that manifest over weeks as opposed to acute toxicities that generally occur within days.

The microfluidic devices of various embodiments describe above allow for direct 3D imaging of fluorescent protein-based biosensors and other fluorescent probes, as well as brightfield imaging of cell morphology. This innovation allows for non-destructive monitoring 28 days or more to measure specific molecular events within cells. The molecular events correspond to clinically significant signatures of drug toxicity and disease state. The molecular mechanisms of toxicity ("MOT") currently monitored in cells and are associated with adverse drug reactions include oxidative stress, mitochondrial dysfunction, bile canalicular efflux inhibition, immune mediated toxicity, and fibrotic scarring. Many other MOTs can be evaluated through the use of fluorescent biosensors. In addition, the in vitro liver model can also be used to model disease states, and disease associated molecular mechanisms of action ("MOA"), for the testing of potentially therapeutic drugs.

Certain embodiments are directed to systems including the microfluidic devices described above and a computer in connection with the one or more sensors, imaging devices, or combinations thereof. The computer may be configured to receive data from the optical system and to store at least a portion of the received data in one or more memory components as at least one database. The computer may be further configured to analyze the images and sensor data received by the memory components and identify particular components of the images such as, damaged, cells, biomarkers, metabolites, and the like and combinations thereof.

Embodiments of the invention include methods for testing the response of cells and tissues enclosed in the housing of the microfluidic devices to exposure to a test substance. Such methods may include the step of introducing one or more reference substances into a microfluidic device with established tissue architecture and detecting a response to the one or more reference substances. Detecting can be carried out by various means including for example, capturing images of the tissue after exposure, detecting biomarkers associated with toxicity or diseases states, and the like and combinations thereof. In some embodiments, the methods may further include constructing a computational model to predict human liver response to exposure to the reference substance. Such modeling may include generating pharmacokinetic and pharmacodynamic (PK/PD) data, identifying toxic substance, and determining efficacy of reference substances for improving a diseased state.

In some embodiments, such methods may include providing a microfluidic device having established architecture of the liver sinusoidal units such as those described above, introducing one or more test materials into microfluidic device, and detecting one or more analytes in the effluent of the microfluidic device. Other methods of embodiments include providing a microfluidic device having established architecture of the liver sinusoidal units such as those described above, introducing one or more test materials into microfluidic device, and capturing images of the architecture of the liver sinusoidal units after introducing the test material into the microfluidic device, and in some embodiments, such images may include analytes. In still other embodiments such methods may include both detecting an analyte and capturing images. The analytes of various embodiments may vary and can be, for example, metabolites of the test material, biomarkers, fluorescent markers from test materials, biomarkers and metabolites associated with a diseased state, cellular debris, and the like and combinations thereof.

In some embodiments, the method may incorporate the use of multi-color fluorescent protein-based biosensors to track physiological functions and their perturbation in real-time. The biosensor cells, also referred to as "sentinel cells," can be created, for example, by integration of the genetic sequence of the biosensor into the host cell genome via lentiviral transduction. Such biosensors are expressed in cells through normal transcription/translation. In various embodiments, the biosensors can be used to monitor cell movement, cell division, apoptosis, reactive oxygen, and calcium flux in mitochondria. Biosensors are stable over the lifetime of cells whereas fluorescent probe dyes can become chemically modified to a non-fluorescent state, and can diffuse, or even be pumped from the cells within hours to days. Protein biosensors have less effect on cell health compared to dyes that are known to produce cytotoxic oxygen radicals when illuminated (photobleaching). The combination of lentiviral delivery, availability of multiple colors of fluorescent proteins and the user-controlled addition of cells to the model lends the flexibility needed to monitor distinct events in different cell types. For example, the generation of reactive oxygen in hepatocytes can be observed while monitoring initial steps leading to fibrotic scarring, such as the stimulation of stellate cell division. Additionally, the biosensors are sensitive and reversible such that abnormal levels of calcium (or other ion) fluxes within a cell are detected, but normal calcium (or other ion) distributions will be indicated when restored to normal levels in the cell.

In some embodiments, the data collected from the microfluidic devices can include biochemical, mass spectroscopy, biosensor cells, readouts from other fluorescent probes, and morphological readouts. Interpretation of the results as indications of potential human liabilities, or therapeutic benefits may include computational models that can predict human drug interactions from the data provided by the organ model. To construct these predictive models data from preclinical, clinical, and post-market drug trials can be compared with the readouts of the microphysiology organ model in a microphysiology database. The drug trial data can be collected from public databases and literature references. These combined data can be used to develop classification models such as random forests, support vector machine, and others that will predict human liver-drug interactions from the microphysiology liver-drug interactions measured from the microfluidic devices.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims. The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

EXAMPLES

Efflux media was collected for measurements of organ model health using assays for lactate dehydrogenase (LDH) release, and albumin, and urea synthesis. LDH is released from cells under conditions of cytotoxic damage. Albumin and urea are secreted from functional hepatocytes. The media efflux was also used to monitor the presence of drug and metabolic products for PK. When compounds are included in the microfluidic media, hepatocytes are exposed to the compound and often biotransform them to a chemically distinct product. Mass spectrometry is a specific and sensitive method to observe these changes. Typically, ca. 15 microliters of media is collected for each biochemical and mass spec measurement (flow rate=5 microliters per hour.)

Example 1

Figure 4:
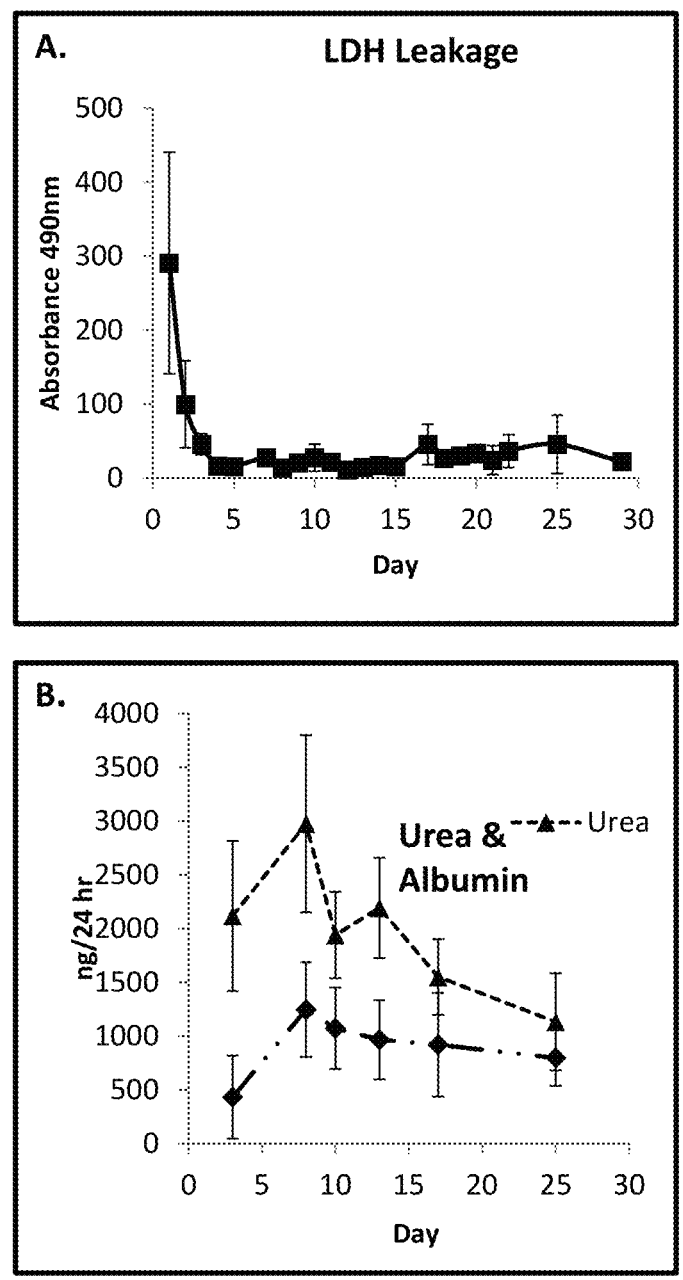
FIG. 4 are data plots showing the long-term health and stability of hepatocytes in the SALA model.

Long-term health and stability of hepatocytes was tested using a microfluidic device with self-assembly liver acinus ("SALA model"), and the results are provided in FIG. 4. Lactate dehydrogenase (LDH) leakage measurements in efflux media are stable from day 2 to day 28 is illustrated in panel A. Panel B shows that urea (top line) and albumin (lower line) output in the efflux media are relatively stable and physiological for over 28 days. Results presented as mean±SD from 3 (days 3, 10 and 17) or 4 devices (days 7, 13 and 25).

Example 2

Figure 5:
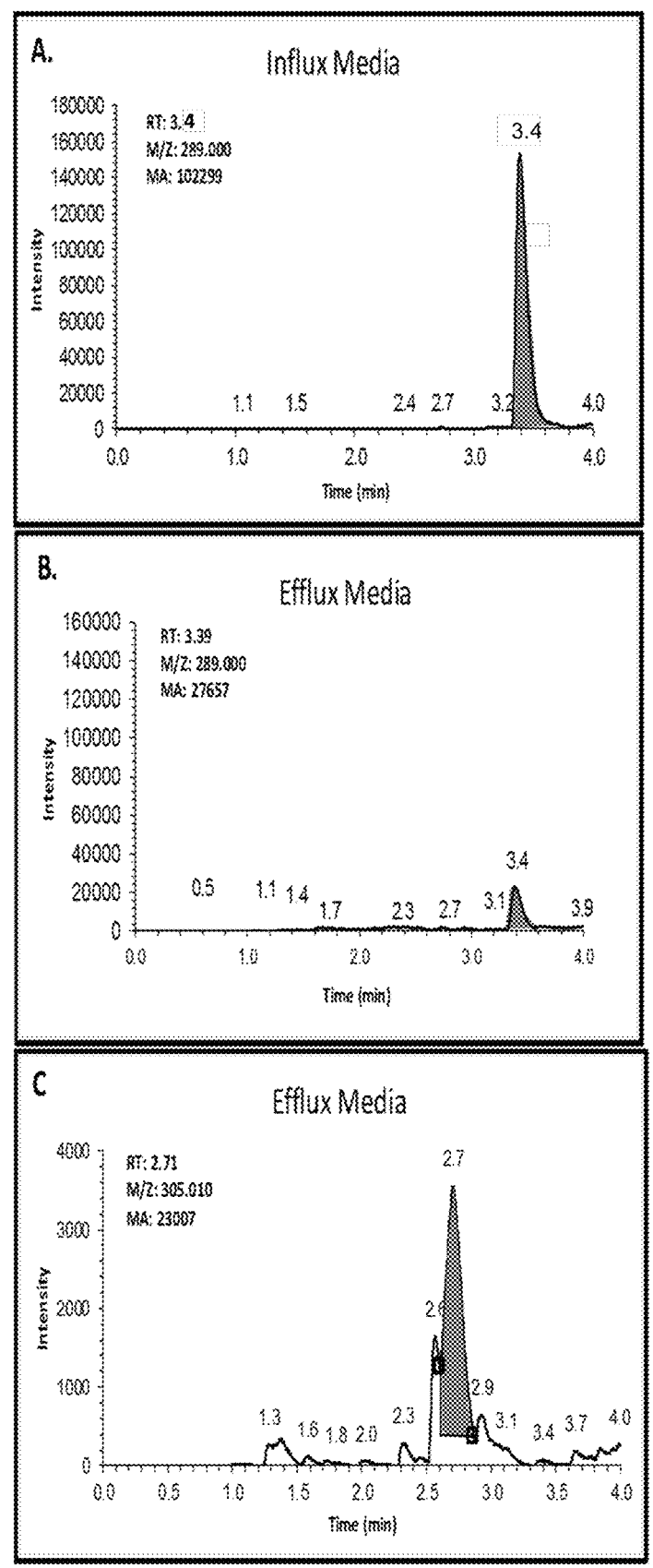
FIG. 5 are liquid chromatography-mass spectrometry chromatograms of metabolic clearance and metabolite production in the SALA model.

Liquid chromotorgraphy—mass spectroscopy ("LC-MS") of effluent was carried out and a chromatogram showing metabolic clearance and metabolite production of SALA model in the microfluidic device on day 10 is provided in FIG. 5. Panel A shows the result of introducing 5 μM testosterone in influx media. Panel B shows testosterone in efflux media collected over 24 hr at 5 μl/hr flow and demonstrates 27% of testosterone exits unchanged through the device as calculated as a ratio of the mass area (MA) under the curves. This value is concordant with testosterone clearance. Panel C shows Cyp3A4 signature metabolite 6-β-hydroxytestosterone in efflux media collected at 5 μl/hr for 24 hr.

Example 3

Figure 6:
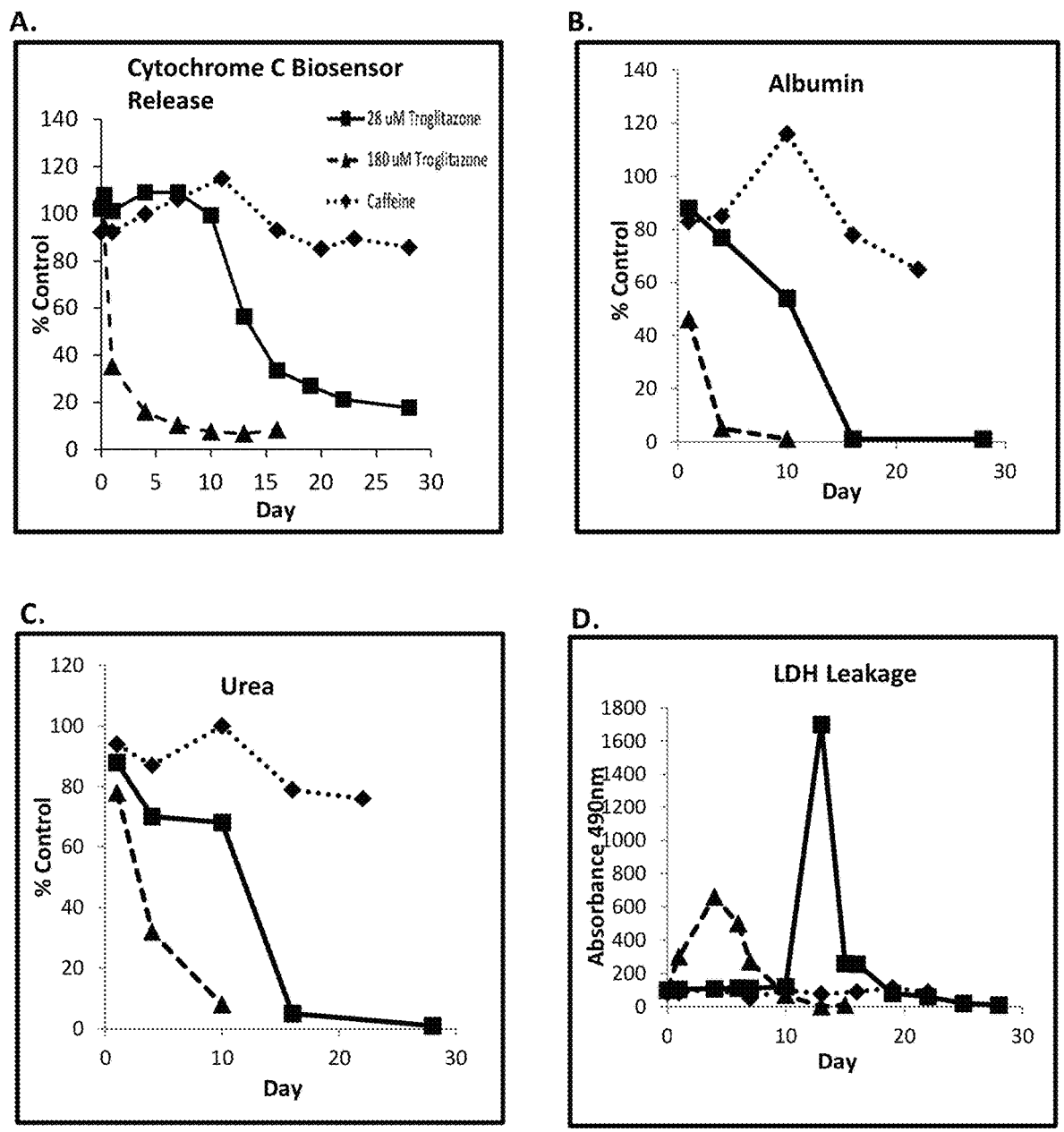
FIG. 6 are data plots form live cell monitoring of hepatocellular cytochrome C release biosensor and biochemical assays performed on the efflux media showing time and dose dependent toxicity an assessment of acute nimesulide toxicity in the SALA model.

Live cell monitoring of hepatocellular cytochrome C release biosensor and biochemical assays performed on the efflux media demonstrates time and dose dependent toxicity is shown in FIG. 6 using the SALA model in a microfluidic device. Troglitazone (28 or 180 μM), or caffeine (600 μM, negative control) was introduced into the microfluidic device for 0-28 days. Troglitazone induces apoptosis in the hepatocytes as indicated by the release of the cytochrome c biosensor in the sentinel cells with a T½ of ~14 days (28 μM) or ~1 day (180 μM) as illustrated in panel A, while caffeine shows no significant effect over 28 days as illustrated in panel B. These data show that troglitazone induces a decline in albumin secretion with a T½ of ~11 days (28 μM) or ~1 day (180 μM), while caffeine shows no significant effect. Troglitazone induces a decline in urea secretion with a T½ of ~12 days (28 μM) or ~3 days (180 μM) as illustrated in panel C, while caffeine shows no significant effect as illustrated in panel D. Troglitazone induces release of LDH with a peak loss at ~13 days (28 μM) or ~4 days (180 μM), while caffeine shows no significant effect. All values are means from two devices.

Example 4

Figure 7:
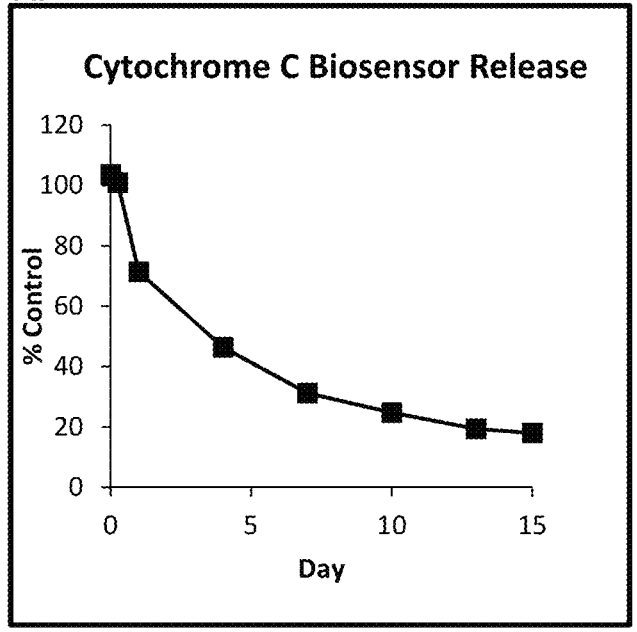
FIG. 7 are data plots showing an assessment of apoptosis resulting from nimesulide toxicity in the SALA model.
Figure 7:
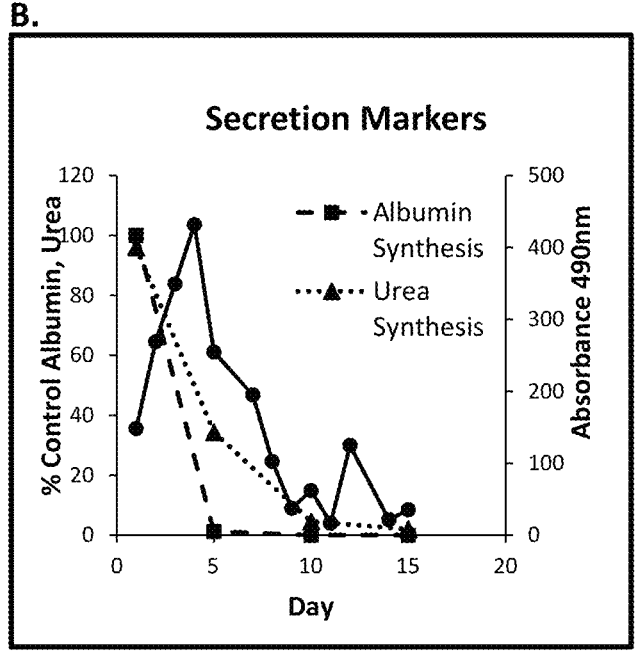

Acute nimesulide toxicity was assessed using the SALA model in a microfluidic device and the results are provided in FIG. 7. Nimesulide (210 μM) induces apoptosis, as indicated by cytochrome C biosensor release, with a T½ of ~3.5 days as illustrated in panel A. LDH leakage also occurred along with induction of apoptosis, and decreases in albumin and urea synthesis, with peak at ~5 days and T½ of 3 and 4 days, respectively, were also observed as illustrated in panel B. All values represent the mean of two liver devices.

Example 5

Figure 8:
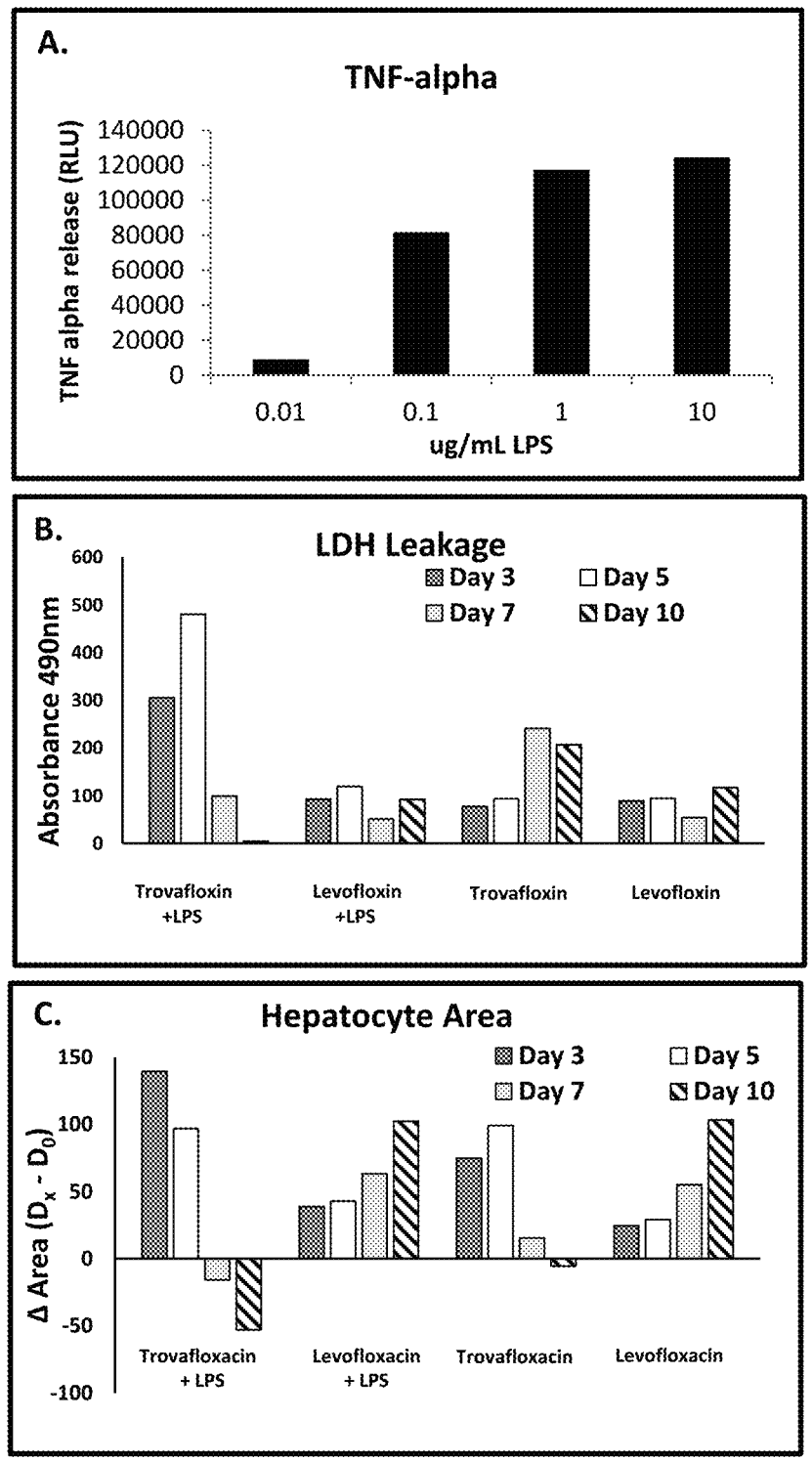
FIG. 8 are data plots showing active immune function in the SALA model.

Active immune function was observed using the SALA model in a microfluidic device, and the results are provided in FIG. 8. Lipopolysaccharide (LPS) activated U937 cells release hepatotoxic TNF-alpha with an EC50 of 0.7 μg/ml as illustrated in panel A. Increased LDH leakage was evident in SALA models treated 3 and 5 days with 200 μM trovafloxacin plus 1 ug/ml LPS or 7 and 10 days with 200 μM trovafloxacin as illustrated in panel B. The shift in toxicity is evident as a decrease in hepatocyte area measured in real-time on days 5 and 7 in the SALA models exposed to 200 μM trovafloxacin plus 1 ug/ml LPS or 200 μM trovafloxacin, respectively, as illustrated in panel C. No hepatocyte area decrease is evident in 600 µM levofloxacin plus 1 ug/ml LPS or 600 µM levofloxacin treated devices as expected. The decrease in hepatocyte area with trovofloxacin plus LPS treatment can be correlated to an increase in propidium iodide uptake. The results are the mean of 2 devices per treatment group.

Example 6

Figure 9:
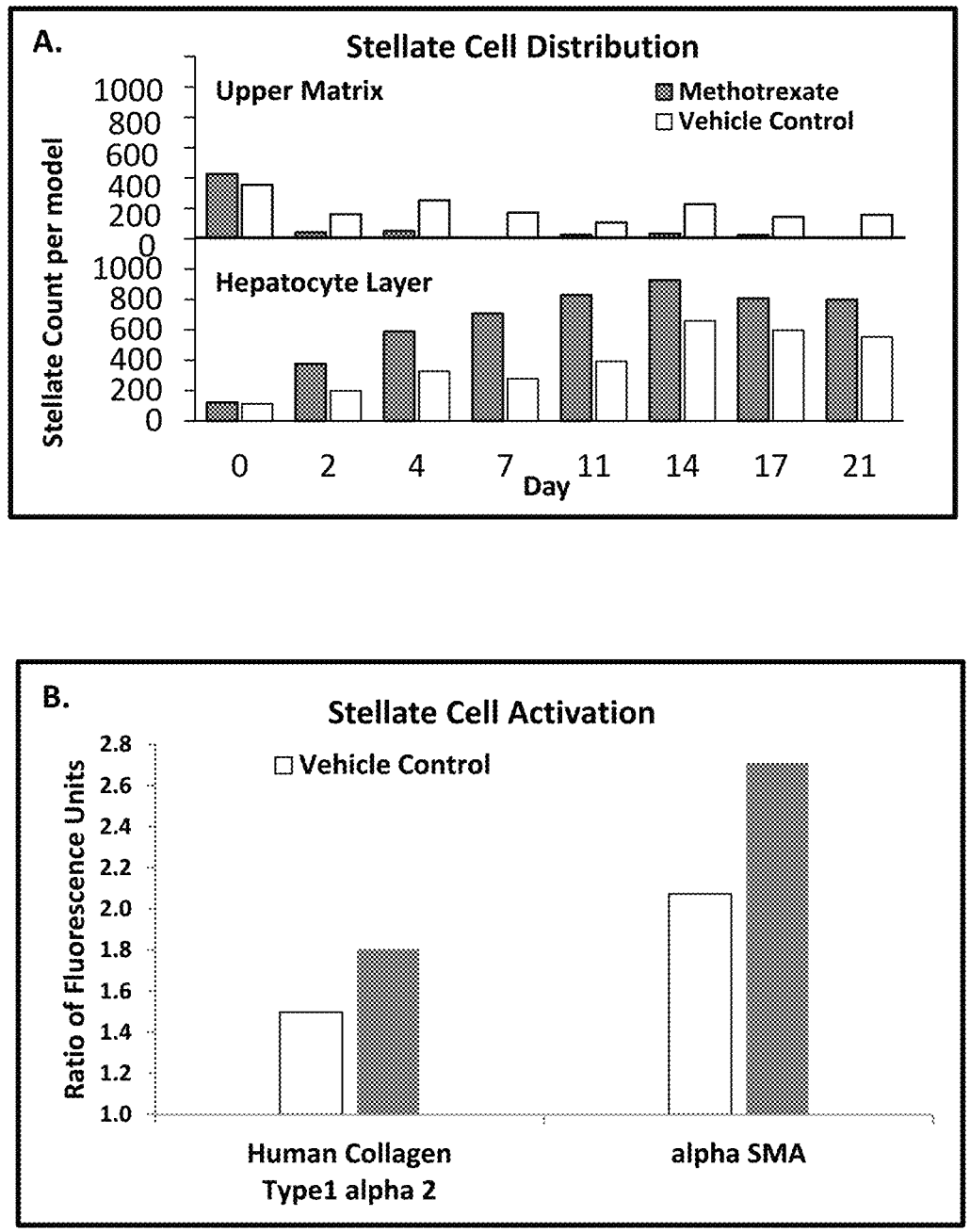
FIG. 9 are data plots showing activation and migration of stellate cells in the SALA model.

LX-2 stellate cell activation and migration in SALA was tested using the SALA model in a microfluidic device, and the results are provided in FIG. 9. In response to 30 nM methotrexate treatment over 21 days, LX-2 stellate cells divide and transmigrate from the upper matrix in the SALA model and accumulate in the lower hepatocyte layer at an accelerated rate compared with vehicle (1.0% DMSO) treatment measured by image analysis of the total SALA model volume as illustrated in panel A. Expression of human α-SMA and collagen type 1A2 proteins in LX-2 stellate cells on day 21, quantitated by image analysis is increased with 30 nM methotrexate treatment, relative to vehicle control is illustrated in panel B.

Example 7

Figure 10:
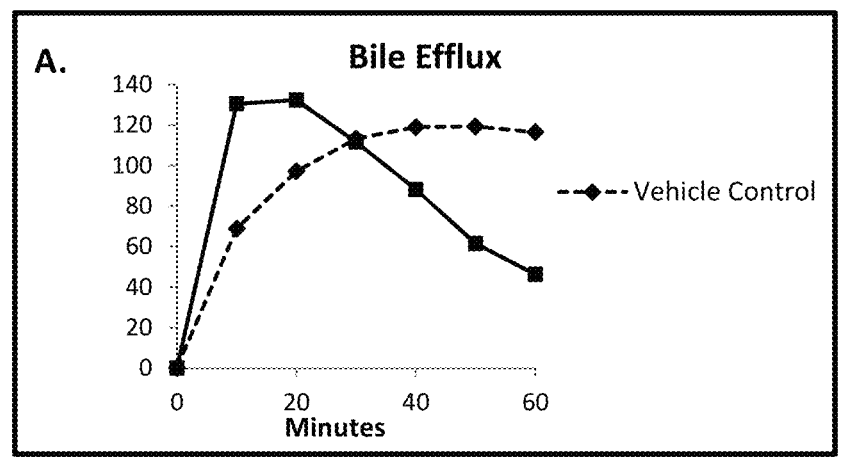
FIG. 10 is a data plot showing bile efflux in vehicle and troglitazone treated SALA model and micrographs showing bile efflux.
Figure 10:
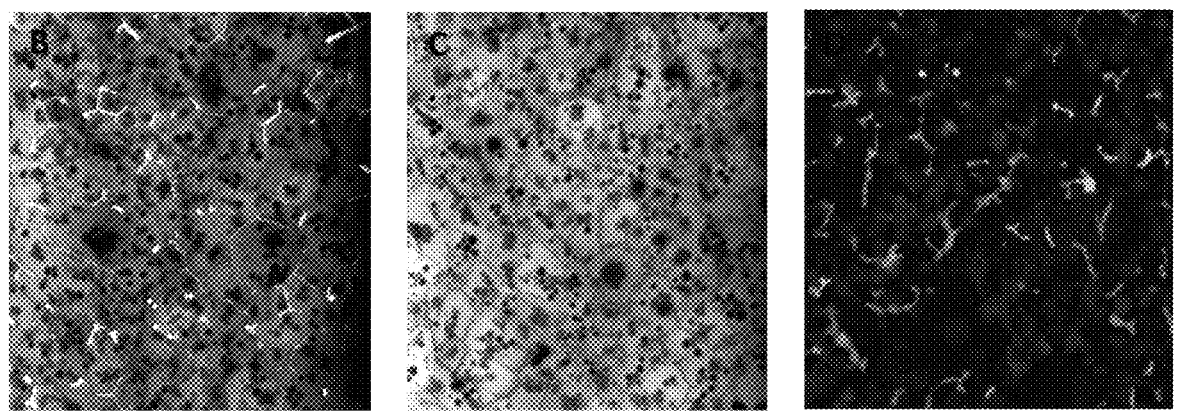

Bile efflux in vehicle and troglitazone treatment was tested using the SALA model in a microfluidic device, and the results are provided in FIG. 10. Panel A shows CMFDA fluorescence monitoring in hepatocytes at 10 minute intervals for 60 minutes in a following 10 day treatment with vehicle control (1% DMSO) or troglitazone (50 µN). Normal uptake and efflux of the dye is evident in vehicle compared to the slower uptake and inhibition of efflux in the troglitazone treated device. Panel B shows a 20X image of vehicle control treated liver model demonstrating normal efflux (white canaliculi) at 60 minutes. Panel C shows the BSEP inhibitor troglitazone (50 µM) d increased hepatocyte retention of dye at 60 minutes. Bile efflux is demonstrated on Day 21 in the SALA under untreated media flow as illustrated in panel D.

Figure 11:
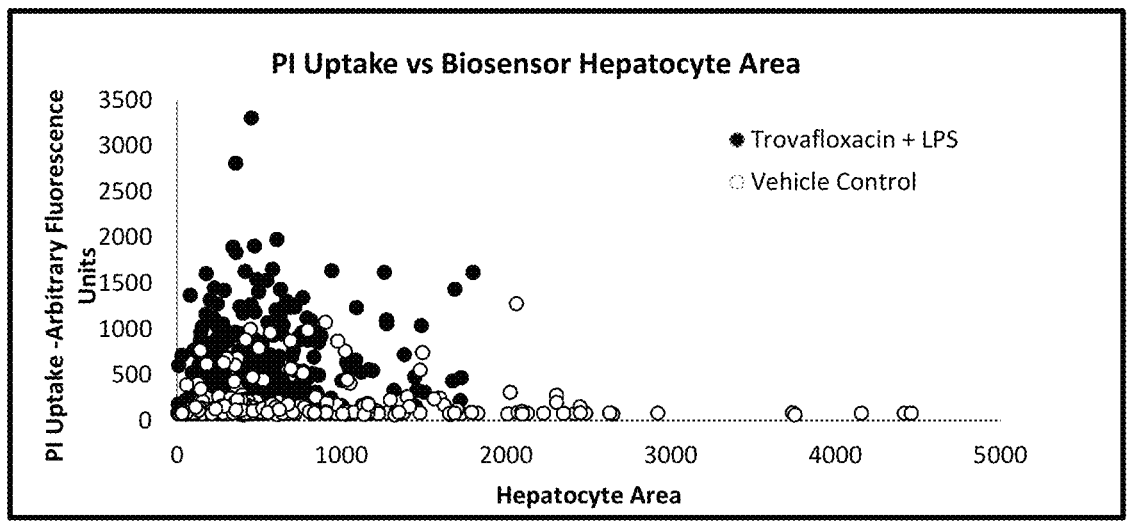
FIG. 11 is data plot showing the correlation of propidium iodide uptake with cell area of hepatocytes in the SALA model.

Correlation of propidium iodide (PI) uptake with cell area of hepatocytes is illustrated in FIG. 11. The cytochrome C biosensor is used to measure hepatocyte area in order to perform real-time measurements of apoptosis. Trovafloxacin (200 µM) co-treated with 1 ug/ml LPS induces toxicity in hepatocytes as noted by a reduction in cell area and increased PI uptake when compared to vehicle (1% DMSO).

Example 8

Figure 12:
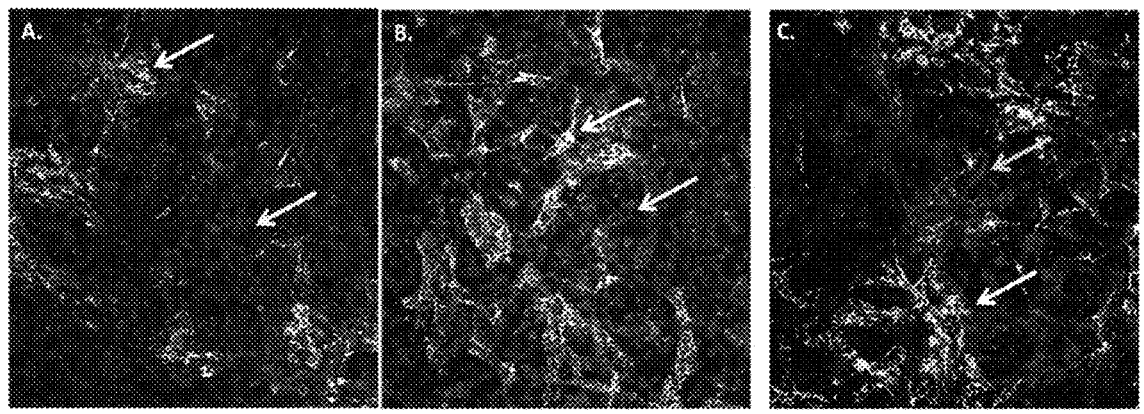
FIG. 12 are micrographs showing stellate cell activation in the SALA model.

LX-2 stellate cell activation was observed using the SALA model in a microfluidic device, and the results are provided in FIG. 12. Immunofluorescence image of a SALA liver exposed to vehicle for 21 days, fixed and reacted to α-SMA antibody is provided in panel A. Minimal α-SMA expression (false colored red) is evident in green stellate cells (white arrow) or in hepatocytes (yellow arrow). Panel B shows immunofluorescence imaging of a SALA liver treated 21 days with 30 nM methotrexate, fixed and reacted against α-SMA antibody. An increased in α-SMA expression (false colored red) is evident by the increased yellow/white color in stellate cells (white arrow) and red color in hepatocytes (yellow arrow). Day 21 Immunofluorescence images of a SALA liver vehicle treated 21 days, fixed, and reacted against α-Human Collagen type 1/2 is provided in panel C. Expression of collagen is identified as increased yellow (white arrow) in stellate cells which are false colored red. Not all stellate cells express high levels of collagen (orange arrow). Nuclei are false colored blue in all images.

Example 9

Figure 13:
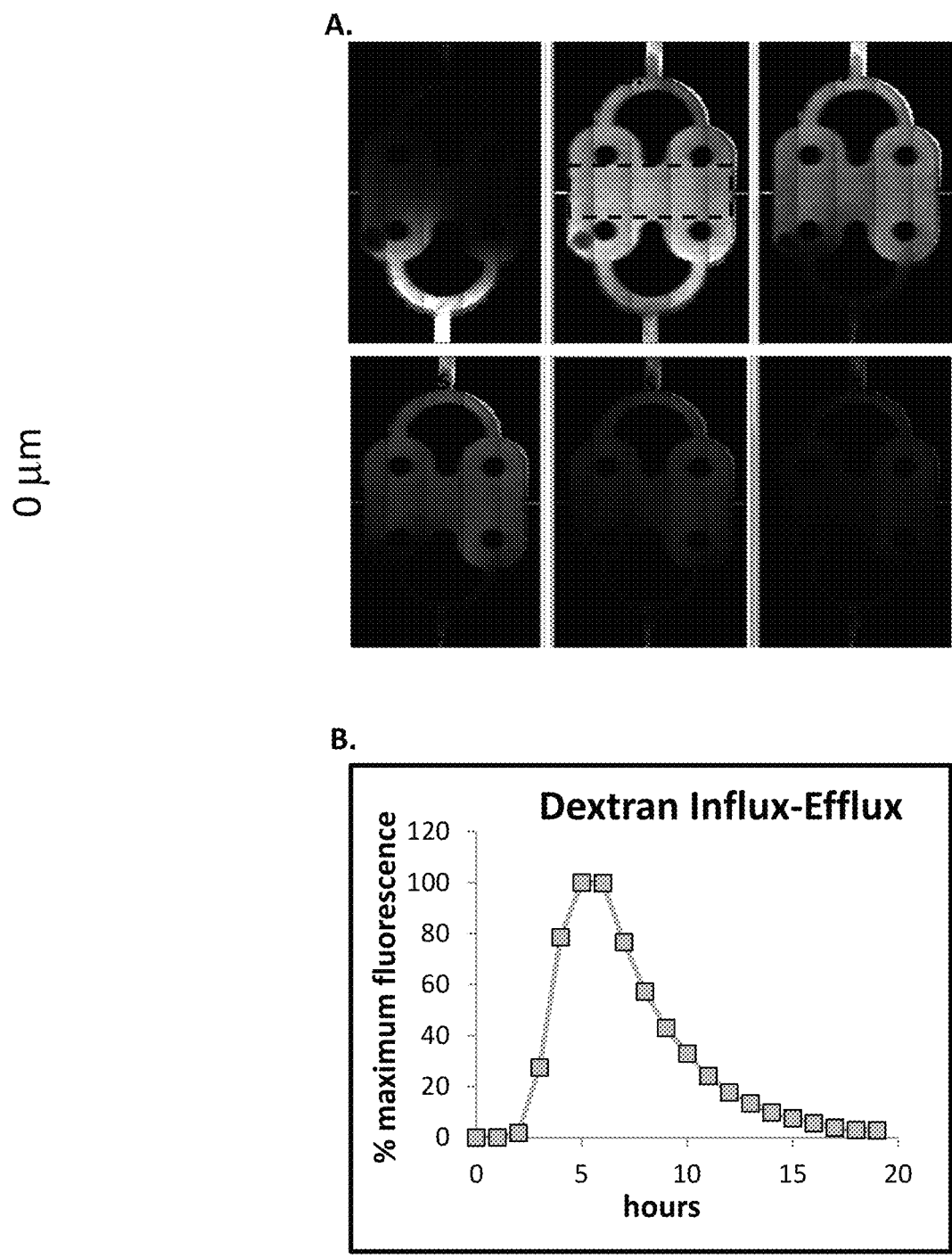
FIG. 13 are micrographs and a data plot showing uniform flow of flow medium through the microfluidic device. Panel A shows fluorescence wash out, and panel B shows a plot of dextran intensity in the effluent.

Demonstration of the uniformity of flow using the SALA model in a microfluidic device is shown in FIG. 13. On Day 7 post-cell seeding, injection of an ~20 µL bolus of 0.1 mg/mL Alexa Fluor® 647-dextran (10 KDa) as a tracer was followed by washout with media flow at 5 uL/hr. The device was imaged at 1 hour intervals on the InCell6000 at 10× magnification. Panel A shows an image sequence (only a subset is shown) showing the uniformity of the influx and washout of fluorescent dextran across the width of the microfluidic device. Panel B shows a graph of the average dextran intensity in the interrogation region (dashed yellow box, A. 6 hrs.) normalized to the maximum value.

Example 10

Statistical validation of biosensors in hepatocyte sentinel cells was carried out and the results are provided in TABLE 1. A panel of biosensors was delivered through lentiviral transduction in multiple fluorescent protein colors initially validated in microplates for an acute response. An SSMD level of ≥2 is considered a statistically valid response.

TABLE 1

| Biosensor | Color Options | Control Compound | Conc (µM) | SSMD |
| --- | --- | --- | --- | --- |
| Nuclear/cell position (Histone H2B) | Blue Green Red | Cell Tracking and Proliferation (Kupffer and Stellate) | — | — |
| Cytochrome C Release: Apoptosis | Green Red | Menadione | 100 | >2 (at 5 hr) |
| Reactive Oxygen Species in Mito. | Green | Menadione | 100 | >2 (at 2.5 hr) |
| Mitochondrial Calcium Uptake | Green | Menadione | 50 | >2 (at 4.5 hr) |
| Steatosis (Label-Free) | White | Tamoxifen | 75 | >6 |
| Bile canalicular efflux (CMFDA) | Green | Troglitazone | 50 | 11 |
| Oxidative Stress in Mito. & Cytoplasm | Blue Green Red | Nefazadone, Menadione | 75 50 | In develop |

Example 11

Figure 14:
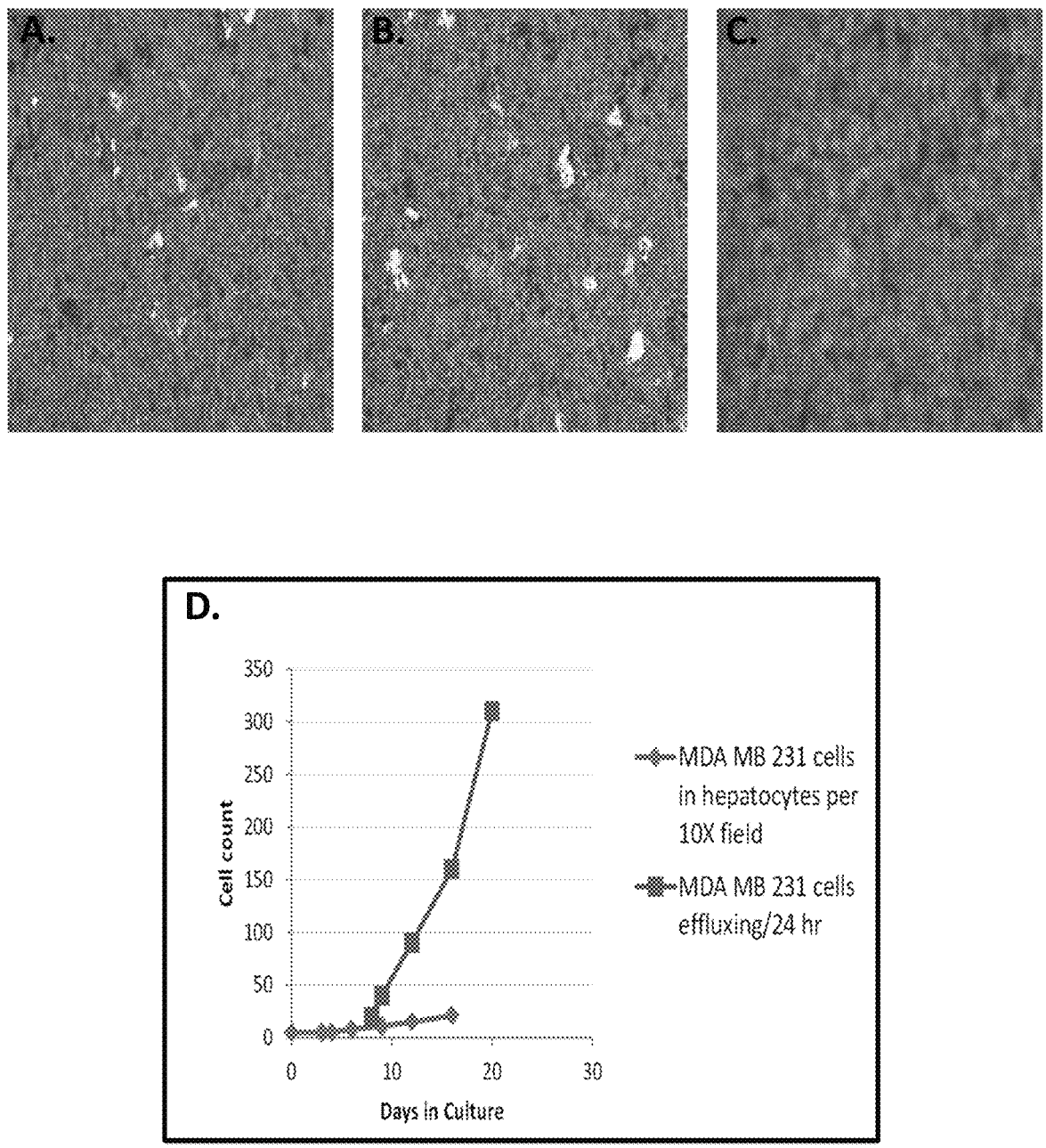
FIG. 14 are micrographs and a data plot showing the maintenance of two subpopulations of cells in the SALA model using a microfluidic device.

MDA-MB-231 cells exhibit two distinct subpopulations in the SALA model in a microfluidic device. One population that is invasive and proliferates and another that is quiescent. These results are provided in FIG. 14 Pane A shows the device a day 3 (10X) with a population of red quiescent MDA-MB-231 cells residing in tissue layer of naïve (gray) and sentinel (green) hepatocytes. Panel B shows the device at day 9 (10X) with a population of red quiescent MDA-MB-231 cells residing in tissue layer of naïve (gray) and sentinel (green) hepatocytes. Panel C shows the device at day 9 (10X) at the same location as shown in panel B but focused on invasive MDA-MB-231 cells in collagen layer above hepatocytes. Green label hepatocytes not shown. Panel D shows red label MDA MB 231 cells collected in the hepatocyte layer from Day 0-16 and counted in the efflux media from Day 8-Day 20. A slow increase in proliferation is evident in the cells residing in the hepatocytes but a rapid increase is evident in the collected efflux. This demonstrates the use of the SALA liver model as a metastatic breast cancer niche to follow the activity of labeled MDA-MB-231 cells, as well as other cancer cells, and the response of the liver micro-environment.

Example 12

Figure 15:
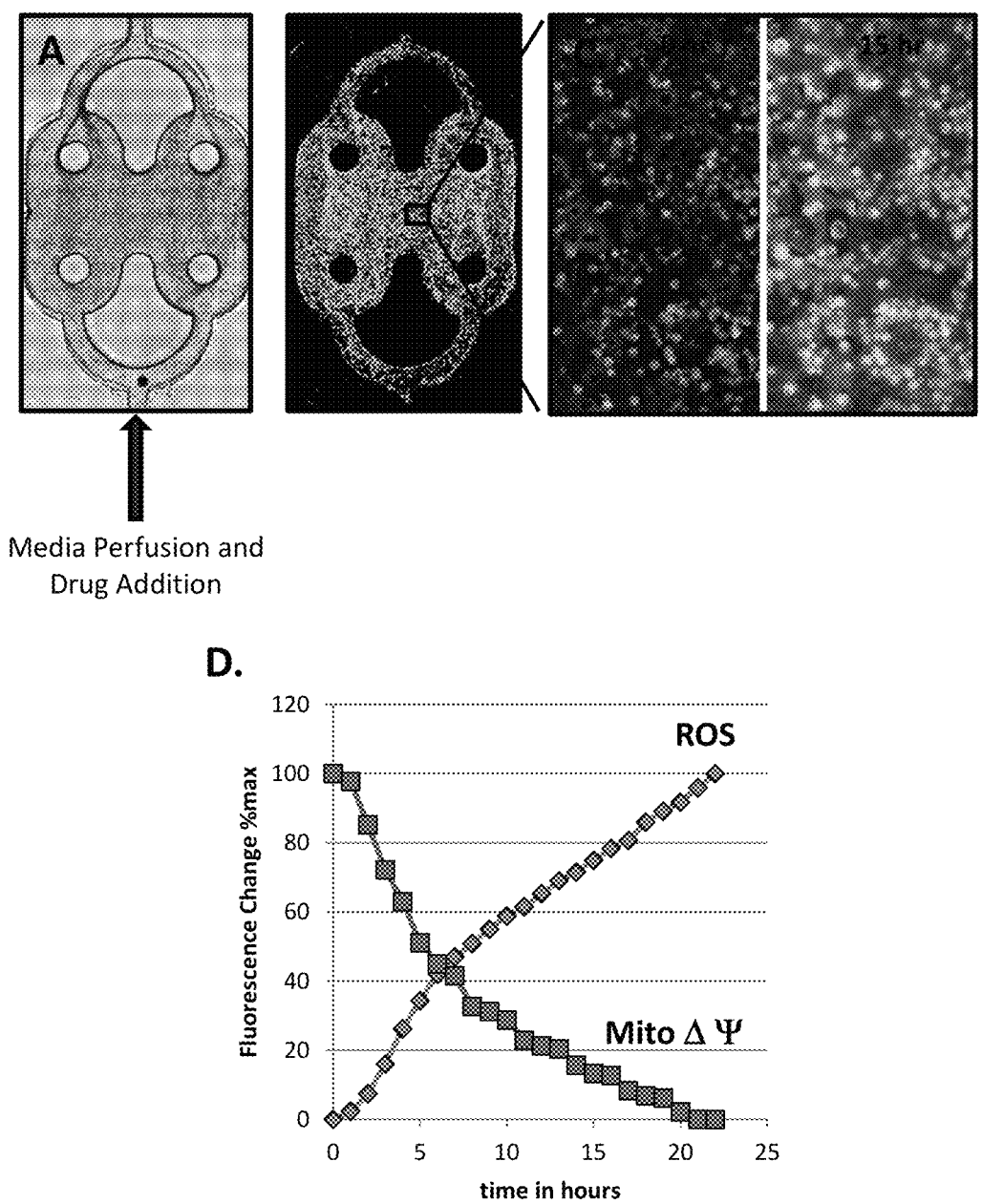
FIG. 15 are micrographs and a data plot showing nefazodone induced oxidative stress response in the SALA model using a microfluidic device.

Nefazodone induces oxidative stress in the SALA model in a microfluidic device, and the results are provided in FIG. 15. Panel A is a montage of brightfield images demonstrating flexibility of HCA instruments to collect and analyze any device layout. Panel B shows biosensor transduced hepatocytes that are viable and well distributed in device. Panel C shows nefazodone induces oxidative stress in the hepatocytes, which can be visualized (½ images presented) as a decrease in mitochondrial function (Red) and increase of ROS generation (Green) at 0 to 15 hr treatment period. Image processing at each time point provides kinetic physiological responses is provided in Panel D.

Example 13

The performance of 4 selected biosensors was tested. One fluorescent readout for bile efflux and control compounds correctly identified hepatotoxic compounds and the mode of toxicity. The results are provided in TABLE 2:

TABLE 2

| Drug | Cmax | Human/Animal Toxicology | Metabolism dependence | MOT | Our Results Negative Weak or late positive Strong Positive |
|---|---|---|---|---|---|
| Trazodone (in use) | 5 uM | extremely rare liver injury Mild ↑transaminases, self eliminating 0.21 incidents/million prescriptions | High clearance drug | No known liver tox | ROS Calcium uptake Mito. membrane potent. Apoptosis bile efflux |
| Nefazodone (withdrawn US) | 0.9 uM | Acute hepatitis Centrilobular (zone 3) necrosis Cholestasis, apoptosis 105 incidents/million prescriptions | High clearance drug, toxic intermediates | Mitochondrial Inhibitor ROS Generation Bile Efflux Inhibition | ROS Calcium uptake Mito. membrane potent. Apoptosis bile efflux |
| Troglitazone (Withdrawn) | 1.8 uM | Moderate to severe ↑ALT, AST Variable necrosis, hepatocellular damage, cholestasis, inflammatory response Up to 1000 incidents/million prescriptions | Impaired clearance | Mitochondrial dysfunction BSEP inhibitor (bile efflux inhibition) | ROS Calcium uptake Mito. membrane potent. Apoptosis bile efflux |
| Menadione (positive control) | Rat 100 mg/kg | Infants: menadione injections produce liver toxicity with hyperbilirubinemia Rat Toxicity (Kidney, Heart, Liver, Lung) IV infusion: Liver: inflammation, degeneration, vacuolization and necrosis MOT identified ROS in liver, calcium uptake into hepatocytes massive liver necrosis in GSH depleted rats | No toxic intermediates known | ROS Mitochondrial Inhibition Calcium uptake | ROS Calcium uptake Mito. membrane potent. Apoptosis bile efflux |

What is claimed is:

1. A microfluidic device comprising:
a housing having at least one inlet and at least one outlet;
extracellular matrix proteins disposed on at least one surface of the housing;
parenchymal hepatic cells dispersed in self-assembled cord formations on the extracellular matrix proteins;
cells of at least two types comprising endothelial cells and immune cells, wherein the parenchymal hepatic cells together with cells of at least two types associated with the extracellular matrix proteins and form three-dimensional structures within the housing; and a flow medium contacting the parenchymal hepatic cells and endothelial and immune cells, wherein the three-dimensional structures are liver acini.

2. The device of claim 1, wherein the parenchymal hepatic cells comprise one or more of cultured hepatocytes, hepatocytes derived from induced pluripotent stem cells, and primary hepatocytes, endothelial cells, immune cells, stellate cells, and combinations thereof.

3. The device of claim 1, further comprising genetically modified cells expressing a genetically encoded fluorescence based biosensors.

4. The device of claim 3, wherein expression of the genetically encoded fluorescence based biosensor is dependent upon calcium levels, pH, glutathione levels, mitochondrial calcium levels, oxidative stress, or reactive oxygen species.

5. The device of claim 3, wherein expression of the genetically encoded fluorescence based biosensor is in response to apoptosis, change in mitochondrial membrane potential, cell proliferation, free calcium ion concentration, cell motility, and oxidative stress response.

6. The device of claim 1, wherein the one or more three-dimensional structures have established zonation.

7. The device of claim 1, further comprising a pump fluidly connected to the inlet configured to propel flow medium through the housing.

8. The device of claim 1, wherein the housing comprises one or more chambers and one or more passages fluidly connecting the chambers.

9. The device of claim 8, wherein the extracellular matrix proteins are disposed in the chambers of the housing.

10. The device of claim 1, further comprising a sensor positioned to detect analytes in effluent exiting the housing.

11. The device of claim 1, further comprising an imager positioned to image the three-dimensional structures.

12. The device of claim 1, further comprising one or more ports positioned to introduce substances into the flow medium.

13. The device of claim 1, wherein the endothelial cells are EAhy.926 endothelial cells and the immune cells are U937 monocytic cells.

14. The device of claim 1, where the endothelial cells and immune cells are dispersed between the cord formations.

15. The device of claim 1, wherein the three dimensional structures are self-assembled.

16. The device of claim 1, further comprising polymerized collagen.

17. The device of claim 1, further comprising stellate cells.

18. The device of claim 1, wherein the stellate cells are LX-2 stellate cells.

19. The device of claim 1, wherein the liver acini are capable of producing bile.

20. A method for self-assembly of three-dimensional structures of liver acini comprising:
providing a surface coated with an extracellular matrix protein;
contacting the surface with parenchymal hepatic cells to form self-assembled cord formations on the extracellular matrix proteins;
incubating the parenchymal hepatic cells for about 12 to about 16 hours in a flow medium;
contacting the surface with endothelial cells and immune cells;
incubating the parenchymal hepatic cells and endothelial and immune cells for about 1 to about 12 hours in a flow medium thereby forming three-dimensional structures of liver ancini; and
contacting the surface with polymerized collagen.

21. The method of claim 20, wherein the surface is disposed within a microfluidic device.

22. The method of claim 20, wherein contacting the surface with polymerized collagen comprises:
introducing collagen into the microfluidic device;
inverting the microfluidic device;
polymerizing the collagen; and
inverting the microfluidic device.

23. The method of claim 20, wherein the parenchymal hepatic cells are genetically modified to express a genetically encoded fluorescence-based biosensor.

* * * * *

UNITED STATES PATENT AND TRADEMARK OFFICE
CERTIFICATE OF CORRECTION

| | |
|---|---|
| PATENT NO. | : 11,060,067 B2 |
| APPLICATION NO. | : 15/515837 |
| DATED | : July 13, 2021 |
| INVENTOR(S) | : D. Lansing Taylor, Albert Gough and Larry Vernetti |

Page 1 of 1

It is certified that error appears in the above-identified patent and that said Letters Patent is hereby corrected as shown below:

In the Specification

Column 1, Lines 24-28: the text "The United States Government may have certain rights to this invention pursuant to Grant No. 1UH2TR00503-01 entitled "A 3D Biomimetic Liver Sinusoid Construct for Predicting Physiology and Toxicity" awarded by the National Institutes of Health.", should read -- This invention was made with government support under TR000503 awarded by the National Institutes of Health. The government has certain rights in the invention. --

Signed and Sealed this
Twelfth Day of November, 2024

Katherine Kelly Vidal
*Director of the United States Patent and Trademark Office*